United States Patent

Sezi et al.

Patent Number: 6,150,558
Date of Patent: Nov. 21, 2000

[54] BIS-O-AMINO(THIO)PHENOLS, AND THEIR PREPARATION

[75] Inventors: Recai Sezi, Röttenbach; Michael Keitmann, Weisendorf, both of Germany

[73] Assignee: Siemens Aktiengesellschaft, Munich, Germany

[21] Appl. No.: 09/161,144

[22] Filed: Sep. 24, 1998

[30] Foreign Application Priority Data

Sep. 24, 1997 [DE] Germany ............ 197 42 195

[51] Int. Cl.[7] .............................. C07C 217/90
[52] U.S. Cl. .............. 564/340; 564/341; 564/346; 564/347; 564/348
[58] Field of Search .................... 564/340, 341, 564/346, 347, 348

[56] References Cited

U.S. PATENT DOCUMENTS 4,525,539  6/1985  Feiring ................. 525/326.3

FOREIGN PATENT DOCUMENTS

| 0023662 | 5/1983 | European Pat. Off. . |
| 0317942 | 5/1989 | European Pat. Off. . |
| 0264678 | 9/1991 | European Pat. Off. . |
| 0300326 | 6/1993 | European Pat. Off. . |
| 195 37 893 A1 | 4/1996 | Germany . |
| 1205518 | 9/1986 | U.S.S.R. . |

OTHER PUBLICATIONS

Chemical Abstract XP–002088350, vol. 106, Mar. 9, 1987, No. 10.
"The Synthesis of 6F Bis(0–Aminophenol) Monomers by a Nucleophilic Substitution Reaction", Jacqueline T. Winzeler et al., Department of Chemistry, Wright State University, Dayton, Ohio 45435, Polymer. Prepr. (Am. Chem. Soc., Div. Polym. Chem.), 34(1), 425–6, 1993.

*Primary Examiner*—Mukund J. Shah
*Assistant Examiner*—Deepak R. Rao
*Attorney, Agent, or Firm*—Herbert L. Lerner; Laurence A. Greenberg; Werner H. Stemer

[57] ABSTRACT

The invention relates to novel bis-o-aminophenols, and bis-o-aminothiophenols of the following structure:

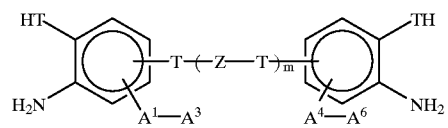

where $A^1$ to $A^6$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$, where at least one of the radicals $A^1$ to $A^6$ must be F or an F-containing group; T is O or S, and m is 0 or 1; and Z is a carbocyclic or heterocyclic aromatic radical.

8 Claims, No Drawings

BIS-O-AMINO(THIO)PHENOLS, AND THEIR PREPARATION

BACKGROUND OF THE INVENTION

Field of the Invention

The invention relates to novel bis-o-aminophenols and bis-o-aminothiophenols, which are also jointly abbreviated to bis-o-amino(thio)phenols, and to a process for their preparation.

Bis-o-aminophenols are needed, in particular, for the preparation of high-temperature-stable polymers, such as polybenzoxazoles (PBOs) and their precursors and for the preparation of hydroxypolyimides (in this respect, see, for example, EP 0 264 678 B1 and EP 0 300 326 B1). PBO precursors can be prepared by reacting a dicarboxylic acid chloride with a bis-o-aminophenol. However, whereas numerous dicarboxylic acids and chlorides thereof are available owing to the wide variety of potential industrial applications, there are comparatively few bis-o-aminophenols. In addition, the nature of the aminophenol used has a strong effect on the property profile of the polymer prepared therewith. For example, not only the thermal, electrical and mechanical behavior, but also the solubility and hydrolysis stability and numerous other properties of the polymer are greatly affected by the aminophenol used in the preparation.

PBO precursors in the form of a photosensitive composition can be structured inexpensively by direct methods, i.e. without an auxiliary resist. Compared with other dielectrics which can be photostructured directly, such as polyimide (PI) and benzocyclobutene (BCB), PBO precursors offer the advantage of positive structurability and aqueous-alkaline development (see EP 0 023 662 B1 and EP 0 264 678 B1). To this end, the PBO precursors used must be substantially transparent at the exposure wavelength and sufficiently soluble in the developer, which preferably contains no metal ions. Like polyimides, polybenzoxazoles also have the major advantage that, compared with the cyclized final product they can be applied to a substrate as readily soluble precursors and then cyclized, during which the solubility and thus the sensitivity to solvents and other process chemicals decreases greatly.

In addition to good electrical, mechanical and thermal properties, use of polybenzoxazoles in microelectronics, in particular as dielectric between two metal planes, for example in multi-chip modules and memory and logic chips, or as buffer coat between the chip and its housing, also requires low moisture absorption; this is because the moisture content in the polymer layer impairs the electrical properties of the polymer and also can result in bubble formation and flaking at high temperatures. A good planarization capacity of the polybenzoxazoles is likewise advantageous since production of components using a dielectric which produces good planarization allows expensive polishing procedures (chemical mechanical polishing, CMP) to be avoided.

Aminophenols which are suitable for the preparation of readily soluble PBO precursors are disclosed, for example, in U.S. Pat. No. 4,525,539 and EP 0 317 942 A2. However, there is no indication therein of the moisture absorption or planarization behavior of the resultant polymers after cyclization on the substrate (see EP 0 264 678 B1 and EP 0 317 942 A2). In the preparation of the aminophenols, a phenolic starting compound is nitrated. If the nitration does not take place completely, i.e. to 100%, and entirely free from isomers, i.e. nitration may only take place in the opposition to the hydroxyl group, reduction of the nitro group in some cases results in aminophenols, which do not allow complete cyclization in the PBO precursor and considerably impair the properties of the polybenzoxazole. This is a major disadvantage of the known preparation processes. SU 1 205 518 A discloses aromatic aminophenols. The preparation of these aminophenols uses carcinogenic hydrazine hydrate, which is a considerable disadvantage. In addition, there is again no indication of the moisture absorption and planarization behavior of the resultant polymers after cyclization on the substrate.

A process for the preparation of bisaminophenols is also disclosed in "Polymer Preprints" 34 (1), 1993, pages 425 and 426. This process has the disadvantage of requiring high temperatures, i.e. significantly higher temperatures than 100° C. (solutions in dimethylacetamide and toluene are refluxed). However, high reaction temperatures promote side reactions, which reduce the yield (which is a maximum of 73%) and make purification of the target product more difficult. In addition, the bisaminophenols so prepared are not stable to oxidation. There is likewise no indication herein of the moisture absorption or planarization behavior of the resultant polymers after cyclization on the substrate.

SUMMARY OF THE INVENTION

The object of the invention is to provide novel bis-o-aminophenols and bis-o-aminothiophenols which are particularly suitable for the preparation of polymers which satisfy the greatly increased demands of microelectronics.

The bis-o-amino(thio)phenols should, in particular, enable the preparation of readily soluble polymer precursors which, after cyclization on a substrate, give polybenzoxazoles or polybenzothiazoles of low moisture absorption, high heat stability and high degree of planarization. In addition, the bis-o-amino(thio)phenols should be stable on storage and should not change on storage in air.

This object is achieved in accordance with the invention by bis-o-aminophenols and bis-o-aminothiophenols of the following structure:

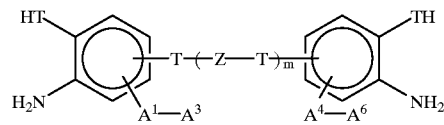

in which $A^1$ to $A^6$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$ where at least one of the radicals $A^1$ to $A^6$ must be F or an F-containing group;

T is O or S, m is 0 or 1; and Z is one of the following carbocyclic or heterocyclic aromatic radicals:

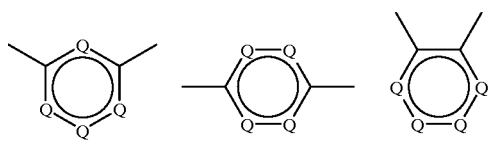

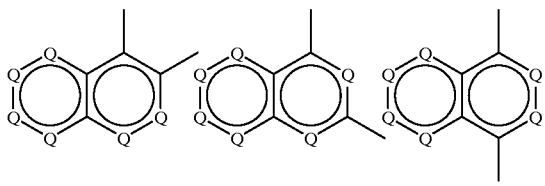
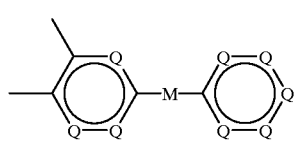

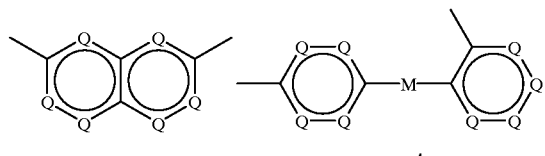

where Q=C—A or N, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$ where p=0 to 8 (linear or branched chain), $OC(CH_3)_3$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, where, in the isolated aromatic rings, a maximum of 3 N-atoms may be present per ring and only 2 N-atoms may be adjacent, and, in the fused ring systems, a maximum of 2 N-atoms may be present per ring, M=a single bond, $(CH_2)_n$, $(CF_2)_n$, $CH(CH_3)$, $CH(CF_3)$, $CF(CH_3)$, $CF(CF_3)$, $C(CH_3)_2$, $C(CF_3)_2$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H_5)$, $C(CF_3)(C_6F_5)$, $C(C_6H_5)_2$, $C(C_6F_5)_2$, CO, $SO_2$,

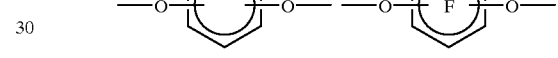
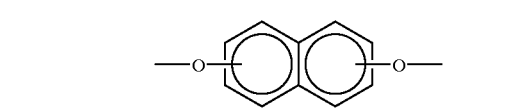

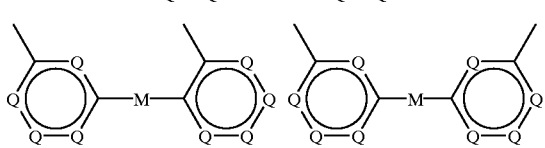

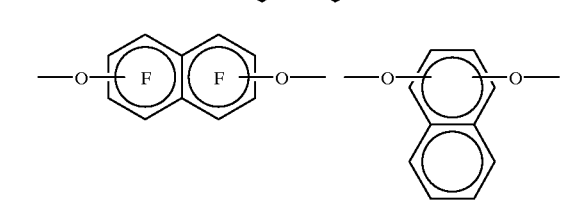

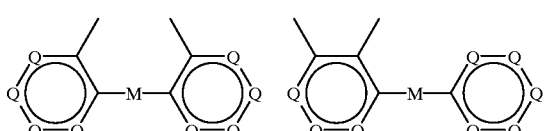

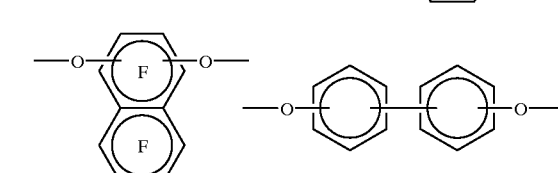

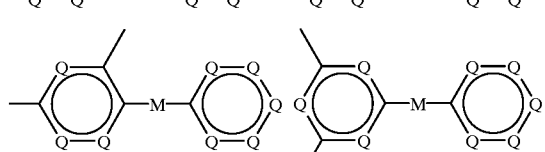

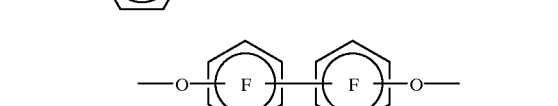

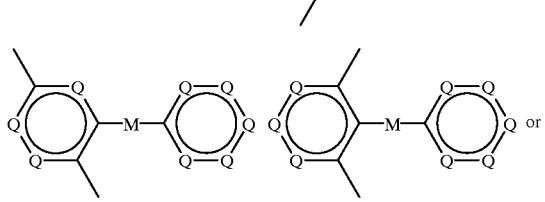

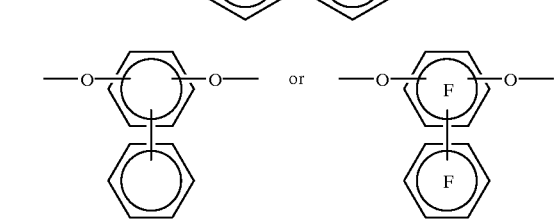

The novel compounds have, for example, the following structure:

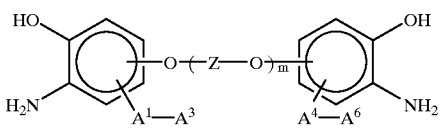

In compounds of this type, the ether bridges are apparently responsible for the good solubility and the good planarization properties of the polymer precursors prepared therewith. By the way, the characterizations "$A^1$–$A^3$" and "$A^4$–$A^6$" in the structural formula means that the aminophenyl groups contain radicals $A^1$, $A^2$ and $A^3$, and $A^4$, $A^5$ and $A^6$ respectively.

The bis-o-amino(thio)phenols are prepared by (a) reacting a nitro compound of the structure

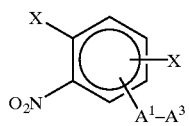

and a nitro compound of the structure

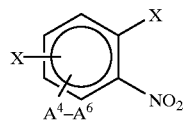

either with an alkali metal hydroxide or alkali metal hydrogensulfide or—in the presence of a base—with a dihydroxy or dimercapto compound of the structure HT-Z-TH or with an alkali metal salt of the dihydroxy or dimercapto compound, in a solvent at a temperature between –10 and 80° C., where X is a halogen atom and $A^1$ to $A^6$, T and Z are as defined above; and (b) reducing the resultant bis-o-nitro(thio)phenol to the bis-o-amino(thio)phenol.

The process of the invention does not give rise to any of the problems which occur in the prior art. The bis-o-amino (thio)phenols prepared by this process additionally have good storage stability and can be stored in air without problems.

DESCRIPTION OF PREFERRED EMBODIMENTS

Preference is given to the preparation of bis-o-amino(thio) phenols in which the substituents $A^1$ and $A^4$, $A^2$ and $A^5$ and $A^3$ and $A^6$ in each case correspond and are arranged in the same position relative to the amino group on the respective phenyl radical. This means that only a single nitro compound is employed in the preparation of these compounds.

The compound HT-Z-TH is an aromatic or substituted aromatic compound (where T=O or S). Suitable compounds for the reaction with the nitro compound are in principle all those in which the hydroxyl or mercapto groups have sufficient nucleophilicity. Examples of such compounds are resorcinol, tetrafluororesorcinol, hydroquinone, tetrafluorohydroquinone, 4,6-dihydroxypyrimidine, 2,4-dihydroxy-5-fluoropyrimidine, octafluorobiphenol, 3,3'-dihydroxy-2,2'-bipyridyl, 2,2-bis(4-hydroxyphenyl)-perfluoropropane (6F-bisphenol A), bis(4-hydroxyphenyl)-sulfone and 2,6-dihydroxyanthraquinone.

The reaction between the dihydroxy or dimercapto compound and the nitro compound, in which ether or thioether bridges are formed, is carried out in the presence of a base. This base is preferably a carbonate or hydrogencarbonate of an alkali metal or alkaline earth metal, such as sodium carbonate or potassium carbonate. For the (thio)ether formation and replacement of the halogen atom (in the opposition to the nitro group) by a hydroxyl or mercapto group, at least stoichiometric amounts of the base are necessary in each case. It may also be advantageous to employ an organic base containing a tertiary N atom, for example triethylamine or pyridine. In this case, the addition of water is necessary. The dihydroxy or dimercapto compound can also be replaced by a corresponding alkali metal salt, for example the potassium salt.

A reaction temperature in the range from –10 to 80° C. has proven suitable. Temperatures not above 80° C. are preferred owing to the greater selectivity of the reaction. This is because the yields here are virtually quantitative, which represents a significant advantage compared to the prior art.

In an advantageous procedure, a temperature of not above 25° C. is initially maintained for some time, for example for about 16 hours, during which the reaction of the nitro compound with the dihydroxy or dimercapto compound takes place. The reaction is subsequently continued at elevated temperature, i.e. at $\geq 40°$ C.; during which replacement of the halogen atom by a hydroxyl or mercapto group then takes place. This procedure selectively gives products in which the hydroxyl or mercapto group is in the opposition to the nitro group.

Suitable solvents are, in particular, dimethylformamide, diethylformamide, dimethylacetamide, dimethyl sulfoxide, N-methylpyrrolidone, y-butyrolactone, acetonitrile, tetrahydrofuran and pyridine. In principle, however, all polar aprotic solvents in which the starting compounds are soluble can be used.

The reduction of the dinitro compound gives the desired bis-o-amino(thio)phenol. The reduction can be carried out, for example, by hydrogenation using hydrogen on Pd/C. In principle, however, all the processes which are suitable for reducing a nitro group to an amino group are suitable. The reduction is preferably carried out at temperatures of from 25 to 50° C. Suitable solvents are esters and ethers, for example ethyl acetate and tetrahydrofuran.

The polymer precursors prepared from the bis-o-amino (thio)phenols of the invention are readily soluble in many organic solvents, such as acetone, ethyl lactate, N-methylpyrrolidone, diethylene glycol mono- or diethyl ether, cyclohexanone and y-butyrolactone, and in aqueous-alkaline developers containing no metal ions. They are therefore highly suitable as base polymers for dielectrics which can be photostructured positively and can be developed in aqueous-alkaline media. The precursors can easily be applied to substrates, such as silicon wafers, by spin-coating methods, they form uniform films, and can readily be cyclized on the substrate. A particular advantage of the precursors prepared from these bis-o-amino(thio)phenols is their high planarization capacity and low moisture absorption.

The invention will be illustrated in greater detail below with reference to working examples.

EXAMPLE 1

Preparation of 2,2-bis[4-(4-nitro-3-hydroxy-2,5,6-trifluorophenoxy)phenyl]hexafluoropropane

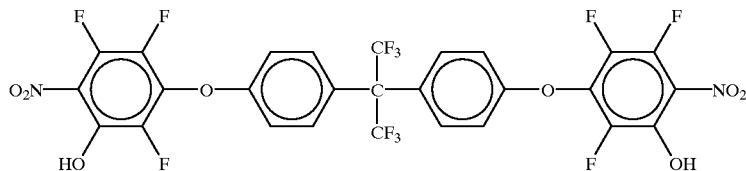

33.6 g of 6F-bisphenol A (0.1 mol) and 42.6 g of pentafluoronitrobenzene (0.2 mol) are dissolved in 400 ml of dimethyl sulfoxide in a 1 l three-neck flask fitted with nitrogen inlet and stirrer. 60 g of potassium carbonate (0.43 mol) are added in portions to the solution. The mixture is then stirred at room temperature for 24 hours, then heated in a temperature-controllable oil bath at 80° C. for 6 hours and, after addition of 10 g of potassium hydrogencarbonate (0.1 mol), for a further 18 hours. The reaction solution is then allowed to cool to room temperature, and the residue is filtered off via a Buchner funnel. After 2 l of water have been added, concentrated hydrochloric acid is added drop wise until the solution is acidic. During this addition, a yellow reaction product precipitates, and is filtered off via a Büchner funnel and washed three times with water. The reaction product is then recrystallized from ethanol and then dried for 48 hours under nitrogen at 40° C/10 mbar in a vacuum drying cabinet (yield: 91).
Characterization:
Mass spectrum: molecular peak at 718
Elemental analysis: Theoretical value (in %): C: 45.1 H: 1.4 N: 3.9. Found (in %): C: 45.1 H: 1.3 N: 3.9
m.p.: 70° C.

EXAMPLE 2
Preparation of 2,2-bis[4-(4-amino-3-hydroxy-2,5,6-trifluorophenoxy)phenyl]hexafluoropropane

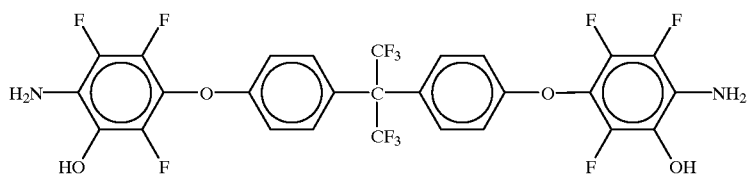

21.5 g of 2,2-bis[4-(4-nitro-3-hydroxy-2,5,6-trifluorophenoxy)phenyl]hexafluoropropane prepared as described in Example 1 (0.03 mol) are dissolved in 200 ml of a mixture of tetrahydrofuran and ethyl acetate (volume ratio 1:1), and 2 g of Pd/C (palladium/ carbon) are added to the solution. The mixture is then hydrogenated at room temperature in an autoclave with vigorous stirring using hydrogen at a pressure of 1 bar; after 2 days, the reaction is terminated. The solution is evaporated to half in a rotary evaporator and left to stand overnight at room temperature, during which the reaction product precipitates in crystalline form. The reaction product is then separated off and dried for 48 hours under nitrogen at 40° C/10 mbar in a vacuum drying cabinet (yield: 93%).
Characterization:
Mass spectrum: molecular peak at 658
Elemental analysis: Theoretical value (in %): C: 49.3 H: 2.1 N: 4.3. Found (in %): C: 49.1 H: 2.2 N: 4.3

EXAMPLE 3
Preparation of 1,4-bis(4-nitro-3-hydroxy-2,5,6-trifluorophenoxy)tetrafluorobenzene

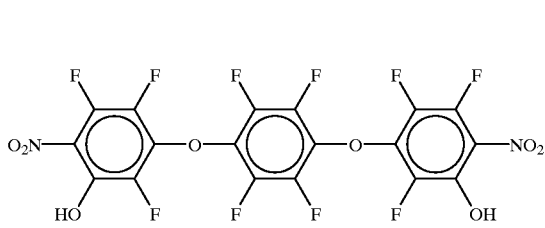

18.6 g of tetrafluorohydroquinone (0.1 mol) and 42.6 g of pentafluoronitrobenzene (0.2 mol) are dissolved in 400 ml of dimethyl sulfoxide in a 2 l three-neck flask fitted with nitrogen inlet and stirrer. 60 g of potassium carbonate (0.43 mol) are added in portions to the solution. The mixture is then stirred at room temperature for 24 hours and then heated in a temperature-controllable oil bath at 60° C. for 4 hours and, after the addition of 30 g of potassium hydrogencarbonate (0.3 mol), for a further 6 hours. The reaction solution is then allowed to cool to room temperature, and the residue is filtered off via a Buchner funnel. After 500 ml of water and 300 ml of ethyl acetate have been added, concentrated hydrochloric acid is added drop wise until the solution is acidic. The organic phase is then washed three times with water, dried over sodium sulfate and evaporated to half in a rotary evaporator. After 2 days, the precipitated yellow crystals are filtered off, washed with methylene chloride and dried for 48 hours under nitrogen at 40° C./10 mbar in a vacuum drying cabinet (yield: 93%).
Characterization:
Mass spectrum: molecular peak at 564
Elemental analysis: Theoretical value (in %): C: 38.3 H: 0.4 N: 5.0. Found (in %): C: 38.4 H: 0.3 N: 4.9
m.p.: 234° C. (decomposition)

EXAMPLE 4
Preparation of 1,4-bis(4-amino-3-hydroxy-2,5,6-tri-fluorophenoxy)tetrafluorobenzene

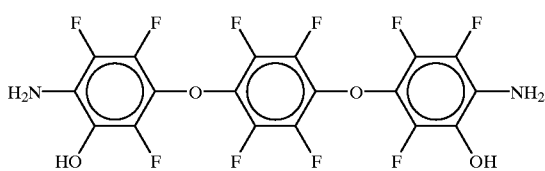

50 g of 1,4-bis(4-nitro-3-hydroxy-2,5,6-tri-fluorophenoxy)tetrafluorobenzene prepared as described in Example 3 (0.09 mol) are dissolved in 500 ml of a mixture of tetrahydrofuran and ethyl acetate (volume ratio 1:1), and 5 g of Pd/C (palladium/carbon) are added to the solution. The mixture is then hydrogenated at room temperature in an autoclave with vigorous stirring using hydrogen at a pressure of 1 bar; after 2 days, the reaction is terminated. The yellow solution is evaporated to half in a rotary evaporator and left to stand overnight at room temperature, during which the reaction product precipitates in crystalline form. The reaction product is then collected and dried for 48 hours under nitrogen at 40° C./10 mbar in a vacuum drying cabinet (yield: 92%).

Characterization:

Mass spectrum: molecular peak at 504

Elemental analysis: Theoretical value (in %): C: 42.9 H: 1.2 N: 5.6. Found (in %): C:41.7 H: 1.3 N: 5.7

EXAMPLE 5

Preparation of 4,6-bis(4-nitro-3-hydroxy-2,5,6-trifluorophenoxy)pyrimidine

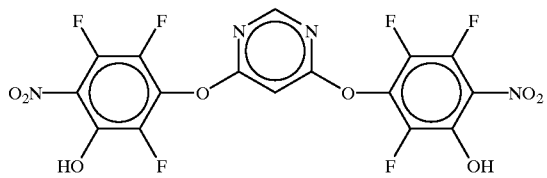

11.2 g of 4,6-dihydroxypyrimidine (0.1 mol) and 42.6 g of pentafluoronitrobenzene (0.2 mol) are dissolved in 400 ml of dimethyl sulfoxide in a 2 l three-neck flask fitted with nitrogen inlet and stirrer. 60 g of potassium carbonate (0.43 mol) are added in portions to the solution. The mixture is then stirred at room temperature for 24 hours and then heated in a temperature-controllable oil bath at 60° C. for 4 hours and, after the addition of 30 g of potassium hydrogencarbonate (0.3 mol), for a further 6 hours. The reaction solution is then allowed to cool to room temperature, and the residue is filtered off via a Büchner funnel. After 500 ml of water and 300 ml of ethyl acetate has been added, concentrated hydrochloric acid is added drop wise until the solution is acidic. The organic phase is then washed three times with water, dried over sodium sulfate and evaporated to half in a rotary evaporator. After 2 days, the precipitated orange-brown crystals are filtered off, washed with petrol ether and dried for 48 hours under nitrogen at 40° C./10 mbar in a vacuum drying cabinet (yield: 94%).

Characterization:

Mass spectrum: molecular peak at 494

Elemental analysis: Theoretical value (in %): C: 38.9 H: 0.8 N: 11.3. Found (in %): C: 39.1 H: 0.7 N: 11.1

EXAMPLE 6

Preparation of 4,6-bis(4-amino-3-hydroxy-2,5,6-tri-fluorophenoxy)pyrimidine

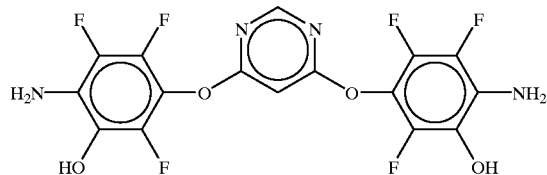

50.8 g of 4,6-bis(4-nitro-3-hydroxy-2,5,6-tri-fluorophenoxy)pyrimidine prepared as described in Example 5 (0.12 mol) are dissolved in 500 ml of a mixture of tetrahydrofuran and ethyl acetate (volume ratio 1:1), and 5 g of Pd/C (palladium/carbon) are added to the solution. The mixture is then hydrogenated at room temperature in an autoclave with vigorous stirring using hydrogen at a pressure of 1 bar; after 2 days, the reaction is terminated. The yellow solution is evaporated to half in a rotary evaporator and left to stand overnight at room temperature, during which the reaction product precipitates in crystalline form. The reaction product is then collected and dried for 48 hours under nitrogen at 40° C./10 mbar in a vacuum drying cabinet (yield: 93%).

Characterization:

Mass spectrum: molecular peak at 434

Elemental analysis: Theoretical value (in %): C: 44.3 H: 1.9 N: 12.9. Found (in %): C: 44.3 H: 1.8 N: 12.8

EXAMPLE 7

Preparation of 4,4'-bis(4-nitro-3-hydroxy-2,5,6-tri-fluorophenoxy)octafluorobiphenyl

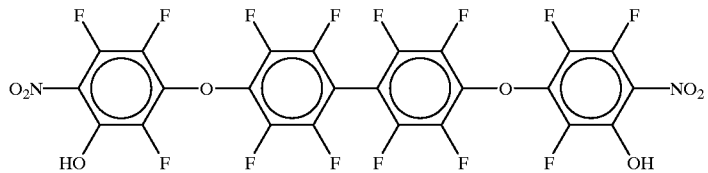

33 g of 4,4'-octafluorobiphenol (0.1 mol) and 42.6 g of pentafluoronitrobenzene (0.2 mol) are dissolved in 400 ml of dimethyl sulfoxide in a 2 l three-neck flask fitted with nitrogen inlet and stirrer. 60 g of potassium carbonate (0.43 mol) are added in portions to the solution. The mixture is then stirred at room temperature for 24 hours and then heated in a temperature-controllable oil bath at 50° C. for 48 hours. The reaction solution is then allowed to cool to room temperature, and the residue is filtered off via a fluted filter. After 500 ml of water and 300 ml of ethyl acetate has been added, concentrated hydrochloric acid is added drop wise until the solution is acidic. The organic phase is then washed three times with water, dried over sodium sulfate and evaporated to half in a rotary evaporator. After 2 days, the precipitated yellow crystals are filtered off, washed with a mixture of methylene chloride and petrol ether (volume ratio 1:1) and dried for 48 hours under nitrogen at 40° C./10 mbar in a vacuum drying cabinet (yield: 90%).

Characterization:

Mass spectrum: molecular peak at 712

Elemental analysis: Theoretical value (in %): C: 40.5 H: 0.3 N: 3.9. Found (in %): C: 40.7 H: 0.4 N: 3.8 m.p.: >300° C.

EXAMPLE 8

Preparation of 4,4'-bis(4-amino-3-hydroxy-2,5,6-tri-fluorophenoxy)octafluorobiphenyl

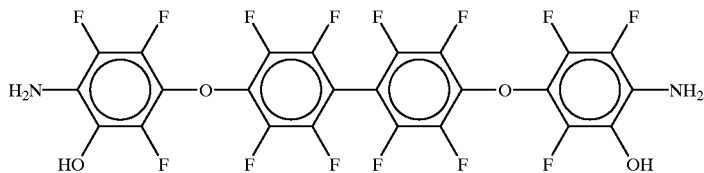

49.8 g of 4,4'-bis(4-nitro-3-hydroxy-2,5,6-tri-fluorophenoxy)octafluorobiphenyl prepared as described in Example 7 (0.07 mol) are dissolved in 500 ml of a mixture of tetrahydrofuran and ethyl acetate (volume ratio 1:1), and 5 g of Pd/C (palladium/carbon) are added to the solution. The mixture is then hydrogenated at room temperature in an autoclave with vigorous stirring using hydrogen at a pressure of 1 bar; after 2 days, the reaction is terminated. The yellow solution is evaporated to half in a rotary evaporator and left to stand overnight at room temperature, during which the reaction product precipitates in crystalline form. The reaction product is then collected and dried for 48 hours under nitrogen at 40° C./10 mbar in a vacuum drying cabinet (yield: 90%).

Characterization:

Mass spectrum: molecular peak at 652

Elemental analysis: Theoretical value (in %): C: 44.2 H: 0.9 N: 4.3. Found (in %): C: 44.0 H: 0.8 N: 4.4

We claim:

1. A bis-o-aminophenol or bis-o-aminothio-phenol of the structure

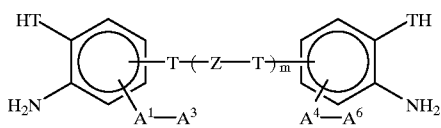

in which $A^1$ to $A^6$ are—independently of one another—H, F, $CH_3$, $CF_3$, $OCH_3$, $OCF_3$, $CH_2CH_3$, $CF_2CF_3$, $OCH_2CH_3$ or $OCF_2CF_3$ where at least one of the radicals $A^1$ to $A^6$ must be F or an F-containing group; T is O or S, m is 0 or 1; and Z is one of the following carbocyclic or heterocyclic aromatic radicals:

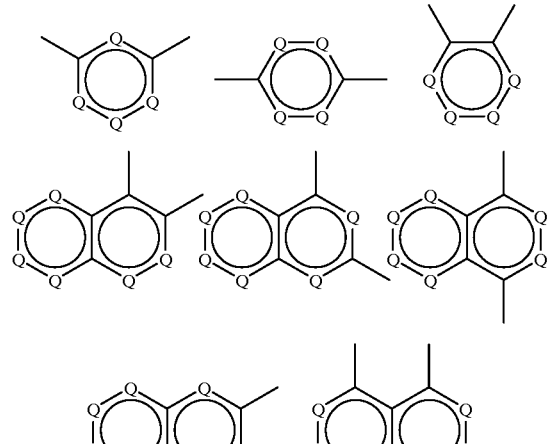

-continued

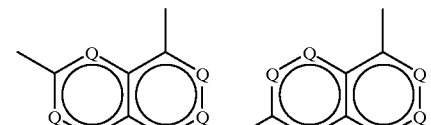
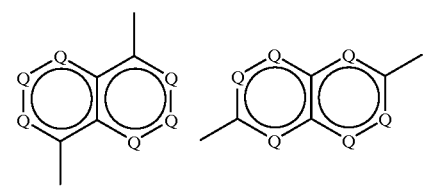
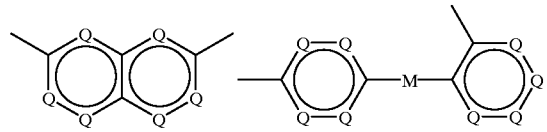
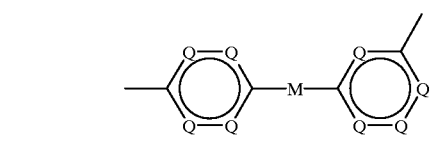
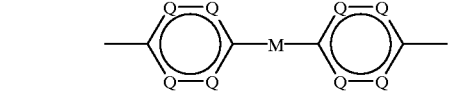
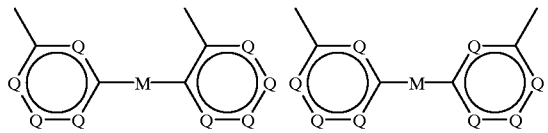
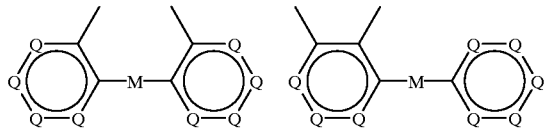
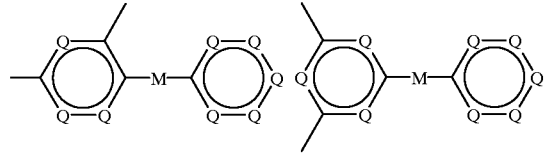
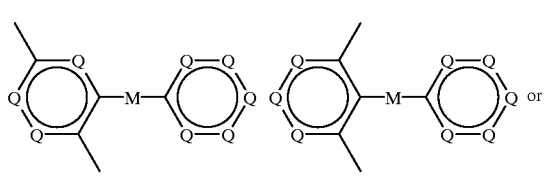

or

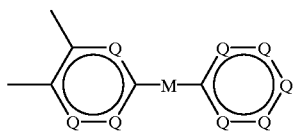

where Q=C—A, and A=H, F, $(CH_2)_pCH_3$, $(CF_2)_pCF_3$, $O(CH_2)_pCH_3$, $O(CF_2)_pCF_3$, $CO(CH_2)_pCH_3$, $CO(CF_2)_pCF_3$ where p=0 to 8 (linear or branched chain), $OC(CH_3)_3$, $OC(CF_3)_3$, $C_6H_5$, $C_6F_5$, $OC_6H_5$, $OC_6F_5$, cyclopentyl, perfluorocyclopentyl, cyclohexyl or perfluorocyclohexyl, where, in the isolated aromatic rings, a maximum of 3 N-atoms may be present per ring and only 2 N-atoms may be adjacent, and, in the fused ring systems, a maximum of 2 N-atoms may be present per ring, M=a single bond, $(CH_2)_n$, $(CF_2)_n$, $CH(CH_3)$, $CH(CF_3)$, $CF(CH_3)$, $CF(CF_3)$, $C(CH_3)_2$, $C(CF_3)_2$, $CH(C_6H_5)$, $CH(C_6F_5)$, $CF(C_6H_5)$, $CF(C_6F_5)$, $C(CH_3)(C_6H_5)$, $C(CH_3)(C_6F_5)$, $C(CF_3)(C_6H_5)$, $C(CF_3)(C_6F_5)$, $C(C_6H_5)_2$, $C(C_6F_5)_2$, CO, $SO_2$,

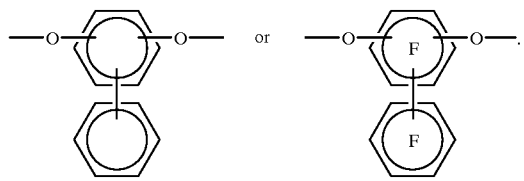

2. A bis-o-aminophenol according to claim 1 having the structure

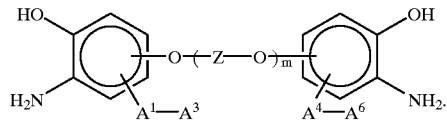

3. A bis-o-aminophenol according to claim 2 in which $A^1$ and $A^4$ are identical, $A^2$ and $A^5$ are identical, and $A^3$ and $A^6$ are identical.

4. A bis-o-aminophenol according to claim 3 in which each of $A^1$ to $A^6$ is a fluorine atom.

5. A bis-o-aminophenol according to claim 2 in which m=1 and Z is a carbocyclic aromatic radical.

6. A bis-o-aminophenol according to claim 2 having the structure

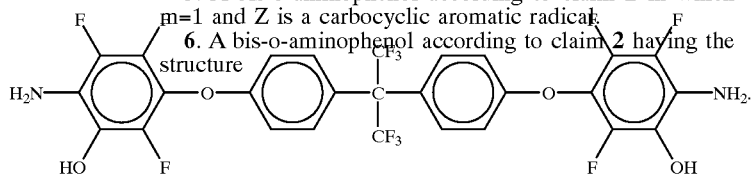

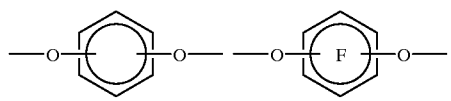

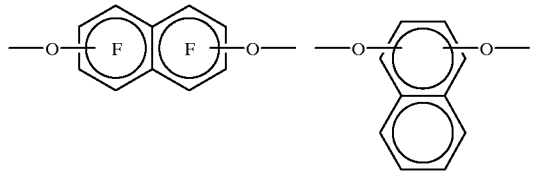

7. A bis-o-aminophenol according to claim 2 having the structure

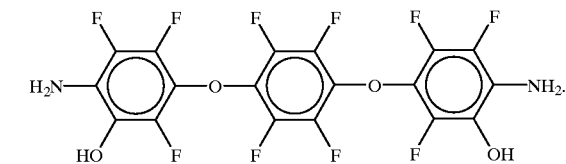

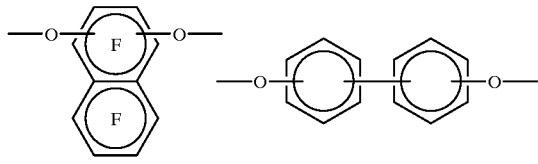

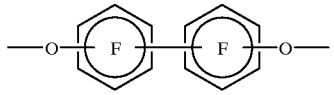

8. A bis-o-aminophenol according to claim 2 having the structure

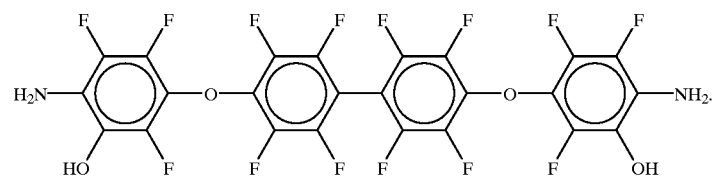
* * * * *